US00PP37170P3

(12) United States Plant Patent
Matsumoto et al.

(10) Patent No.: US PP37,170 P3
(45) Date of Patent: Dec. 23, 2025

(54) ***CITRUS* L. PLANT NAMED 'HAYASE'**

(50) Latin Name: ***Citrus* sp.**
Varietal Denomination: HAYASE

(71) Applicant: NATIONAL AGRICULTURE AND FOOD RESEARCH ORGANIZATION, Ibaraki (JP)

(72) Inventors: Ryoji Matsumoto, Nagayo-sho (JP); Toshio Takahara, Uto (JP); Terutaka Yoshioka, Koshi (JP); Naofumi Hiehata, Sasebo (JP); Takeshi Kuniga, Takamatsu (JP); Atsushi Imai, Higashihiroshima (JP); Satoshi Ota, Shizuoka (JP); Hiroshi Fukamachi, Shizuoka (JP); Keisuke Nonaka, Shizuoka (JP); Hiroko Hamada, Shizuoka (JP); Shingo Goto, Shizuoka (JP); Ayami Hisanaga, Shizuoka (JP); Tomoaki Watanabe, Shizuoka (JP)

(73) Assignee: NATIONAL AGRICULTURE AND FOOD RESEARCH ORGANIZATION, Tsukuba (JP)

( * ) Notice: Subject to any disclaimer, the term of this patent is extended or adjusted under 35 U.S.C. 154(b) by 0 days.

(21) Appl. No.: 19/037,025

(22) Filed: Jan. 24, 2025

(65) Prior Publication Data

US 2025/0351751 P1 Nov. 13, 2025

(30) Foreign Application Priority Data

May 8, 2024 (JP) ..... PVP37416

(51) Int. Cl.
*A01H 5/08* (2018.01)
*A01H 6/78* (2018.01)

(52) U.S. Cl.
USPC ..... Plt./202
CPC ..... *A01H 6/785* (2018.05); *A01H 5/08* (2013.01)

(58) Field of Classification Search
USPC ..... Plt./202, 201
CPC . A01H 5/08; A01H 5/00; A01H 6/785; A01H 6/78
See application file for complete search history.

(56) References Cited

U.S. PATENT DOCUMENTS

PP31,146 P3 * 12/2019 Yoshioka ..... A01H 6/785 Plt./201

* cited by examiner

*Primary Examiner* — June Hwu
(74) *Attorney, Agent, or Firm* — Seckel IP, PLLC

(57) ABSTRACT

A new variety of *Citrus* sp. tree 'HAYASE' that has medium tree habit in-between upright and spreading, spindle-shaped leaf blade with acuminate apex and acute base, vestigial wing, fruit with high diameter/height ratio (average 1.31) and medium to heavy weight (average 152.3 g), no neck, a flat distal part, bright orange (JHS 1305) skin color, thin peel thickness, easy to medium peeling, deep orange (JHS 1307) color when fresh, juicy when fresh, high sweetness, very few seeds, early maturity, and low acidity.

5 Drawing Sheets

Common name: Mandarin.
Botanical classification: *Citrus* sp.
Variety denomination: 'HAYASE'.

BACKGROUND OF THE NEW VARIETY

The present invention relates to a new and distinct variety of Mandarin, *Citrus* sp., which has been given the variety denomination 'HAYASE'.

ORIGIN OF THE VARIETY

The parent varieties are 'TSUNONOZOMI' (female parent) (not patented in the U.S.), and 'SETOKA' (male parent) (not patented in the U.S.) respectively.

The variety was developed and propagated in Minami-Shimabara, Nagasaki, Japan.

The variety was reproduced asexually by vegetative reproduction by top grafting one-year-old scions on rootstocks, also in Minami-Shimabara, Nagasaki, Japan. The rootstock used was satsuma mandarin (not patented) as an interstock grafted onto *Poncirus trifoliata* (trifoliate orange).

In 2001, the parent varieties were crossed. Seeds were collected to be grown in the next year.

In 2002, seeds were grown and seedlings were grafted on top of 'Shiikuwasha' rootstock.

In 2005, first fruiting was observed.

In 2008, preliminary individual selection and characteristics evaluation were performed. Selected plants were grafted on top of satsuma mandarin interstock.

In 2017, the plant was named 'Kankitsu kuchinotsu 53' as a provisional name for a promising breeding line. Growing tests for local adaptability were started under confidentiality conditions.

In 2023, breeding was completed with DUS status confirmed (distinct, uniform, and stable), whereby it was confirmed that the instant tree reproduces true to type in successive generations of asexual reproduction.

In 2024, the variety was named 'HAYASE' and PVP application No. 37,416 was filed on May 8, 2024 in the Plant Variety Protection Office in Japan, whose content is incorporated by reference herein in its entirety.

Cultivation of the variety does not require special conditions or treatments.

The variety is currently mainly intended for fruit production.

SUMMARY OF THE VARIETY

This new mandarin plant 'HAYASE' has tree habit in-between upright and spreading, spindle-shaped leaf blade with acuminate apex and acute base, vestigial wing, fruit with high diameter/height ratio (average 1.34) and medium weight (average 149.9 g), no neck, a flat distal part, bright orange (JHS 1305) skin color, thin peel thickness, easy to medium peeling, deep orange (JHS 1307) color when fresh, juicy when fresh, high sweetness, very few seeds, early maturity, and low acidity.

Specifically, Table 1 below shows a comparison between the instant variety 'HAYASE' and the female parent 'TSUNONOZOMI' as follows (evaluation based on averages):

TABLE 1

Comparison between 'HAYASE' and 'TSUNONOZOMI'

| No. | Characteristics | Female parent 'TSUNONOZOMI' Descriptions | Present variety 'HAYASE' Descriptions |
|---|---|---|---|
| 9 | One year old shoot: spine (number of spines per leaf nodes) (%) | medium (16%) | few (5%) |
| 46 | Style shape | curved | straight |
| 51 | Fruit: shape of distal part | sinking | flattened |
| 85 | Seeds | few to medium (6.2 seeds/fruit) | very few (0.8 seeds/fruit) |
| 87 | Polyembryony | absent | present |

Table 2 below shows a comparison between the instant variety 'HAYASE' and the male parent 'SETOKA', which is also a comparative variety.

TABLE 2

Comparison between 'HAYASE' and 'SETOKA'

| No. | Characteristics | Reference variety 'SETOKA' Descriptions | Present variety 'HAYASE' Descriptions |
|---|---|---|---|
| 9 | One-year old shoot: spine (number of spines per leaf nodes) (%) | many (62%) | few (5%) |
| 44 | Pollens | few | none |
| 46 | Style shape | curved | straight |
| 62 | Fruit weight | heavy (209.1 g) | medium (149.9 g) |
| 84 | Acidity | medium to high (1.34 g/100 ml) | low (0.90 g/100 ml) |

The fruit of 'HAYASE' having few spines on a one year old shoot, no pollen, a straight-style shape, medium to heavy weight, and low acidity, distinguishes it notably from comparative variety 'SETOKA' (not patented in US) having many spines on one year old shoot, few pollens, a curved-style shape, heavy weight, and medium to high acidity.

Table 3 below shows a comparison between the instant variety 'HAYASE' and the comparative variety 'ASUMI' (not patented in U.S.).

TABLE 3

Comparison between 'HAYASE' and 'ASUMI'

| No. | Characteristics | Reference variety 'ASUMI' Descriptions | Present variety 'HAYASE' Descriptions |
|---|---|---|---|
| 9 | One-year old shoot: spine (number of spines per leaf nodes) (%) | intermediate (29%) | few (5%) |
| 44 | Pollens | medium | none |
| 46 | Style shape | curved | straight |
| 84 | Acidity | medium (1.23 g/100 ml) | low (0.90 g/100 ml) |
| 87 | Polyembryony | absent | present |

Table 4 below shows a comparison between the instant variety 'HAYASE' and the comparative variety 'ASUKI' (U.S. Plant Pat. No. 31,146 P3).

TABLE 4

Comparison between 'HAYASE' and 'ASUKI'

| No. | Characteristics | Reference variety 'ASUKI' Descriptions | Present variety 'HAYASE' Descriptions |
|---|---|---|---|
| 44 | Pollens | few | none |
| 46 | Style shape | curved | straight |
| 84 | Acidity | medium to high (1.30 g/100 ml) | low (0.90 g/100 ml) |
| 87 | Polyembryony | absent | present |
| 91 | Time of maturity of fruit for consumption | late (March) | early (January) |

BRIEF DESCRIPTION OF THE DRAWINGS

In the accompanying drawings, which are as nearly true as is reasonable possible to make in a color illustration of this type.

Figure 1:
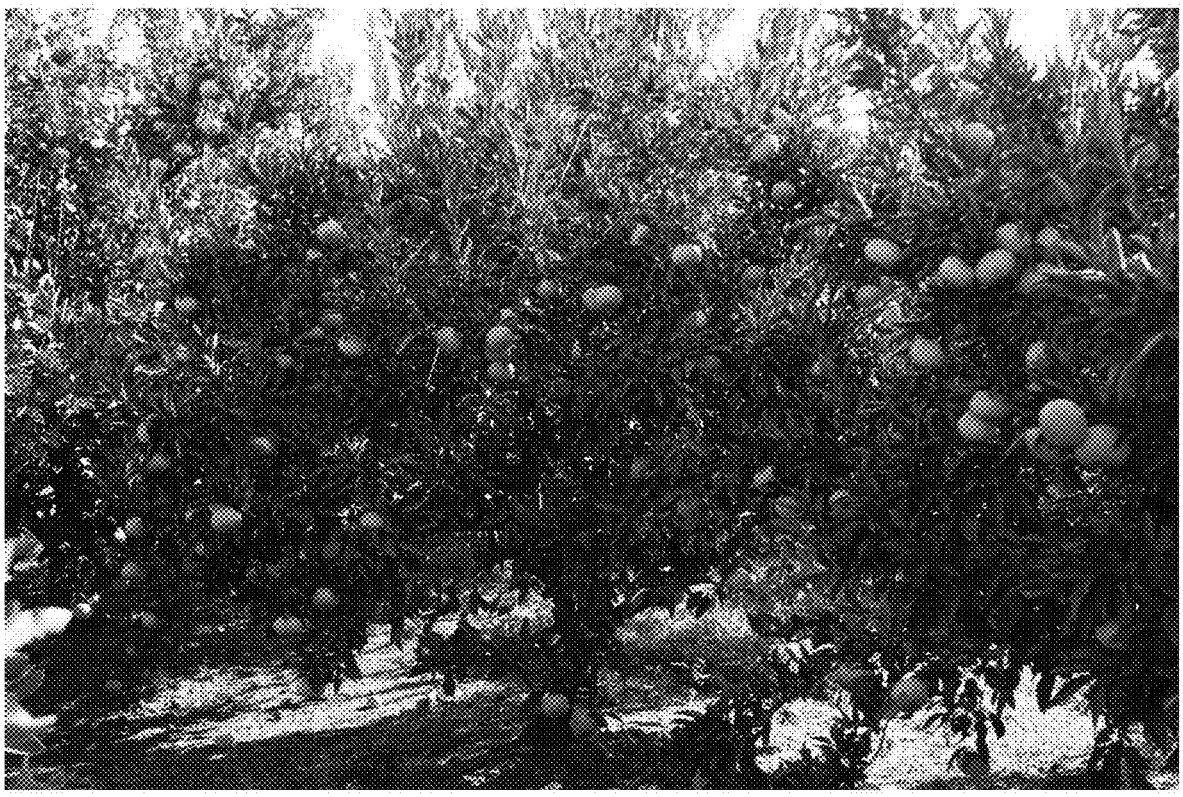
FIG. 1 is a color photograph showing a general view of an illustrative mandarin tree of the variety named 'HAYASE' bearing fruits.
Figure 2:
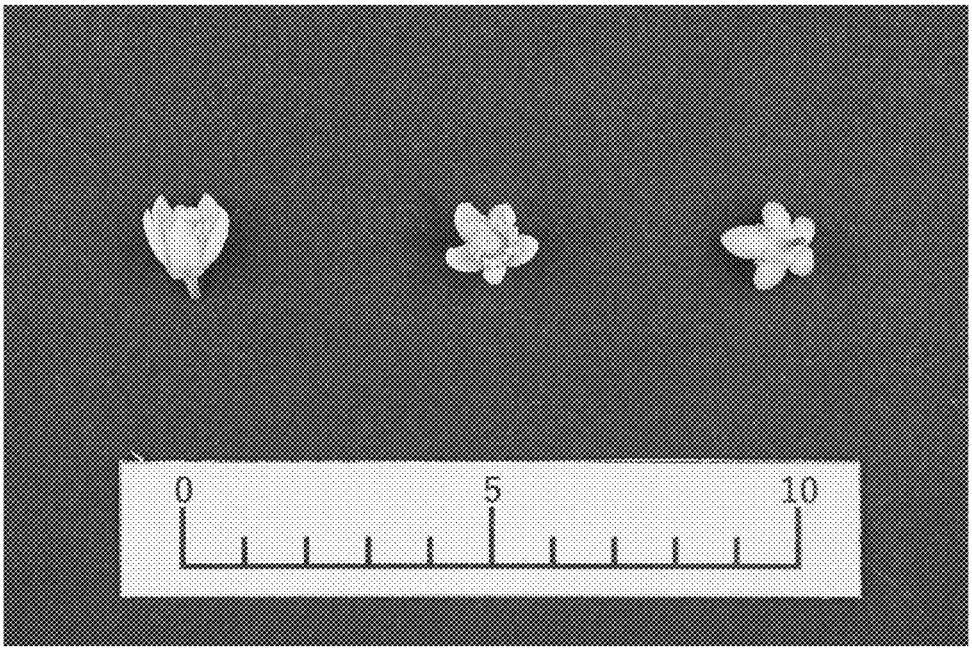
FIG. 2 is a color photograph showing flowers of 'HAYASE'.
Figure 3:
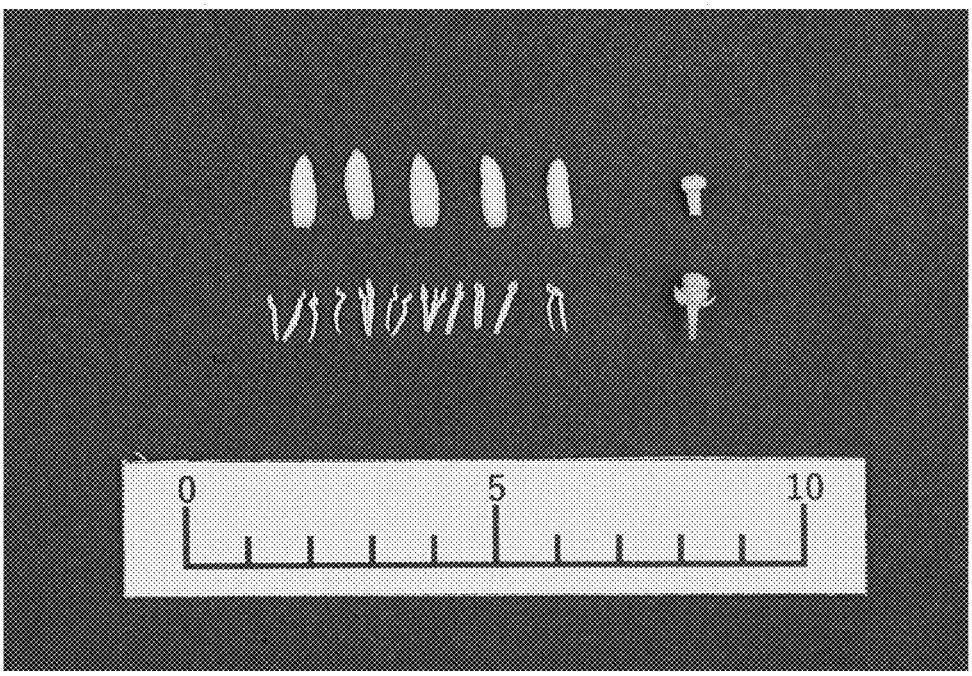
FIG. 3 is a color photograph showing flower organs of 'HAYASE'.
Figure 4:
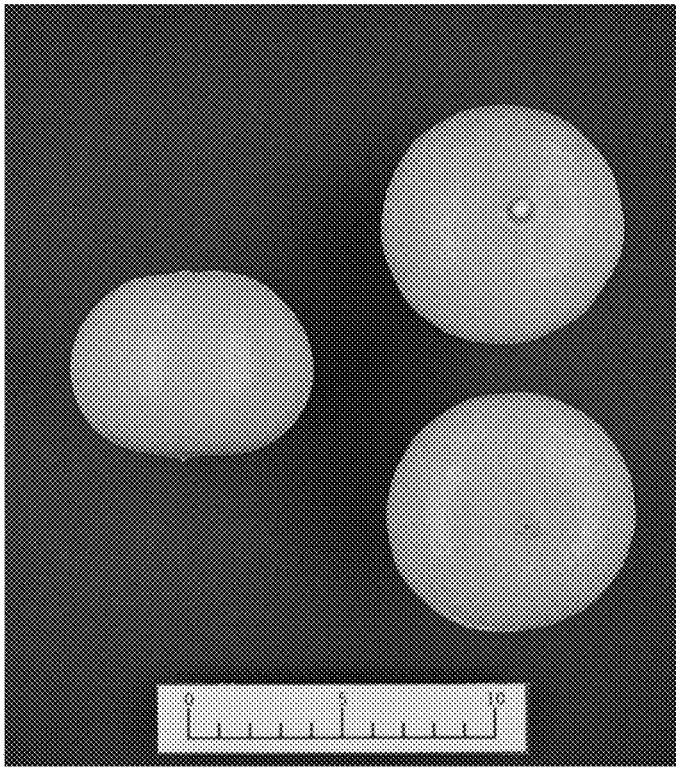
FIG. 4 is a color photograph showing fruits of 'HAYASE'.
Figure 5:
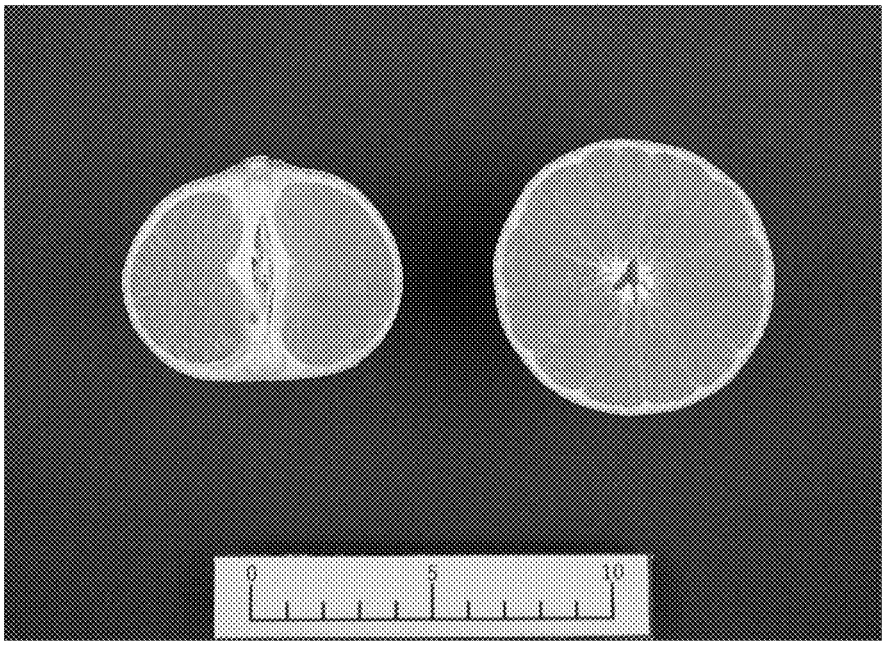
FIG. 5 is a color photograph showing sections of fruit of 'HAYASE'.
Figure 6:
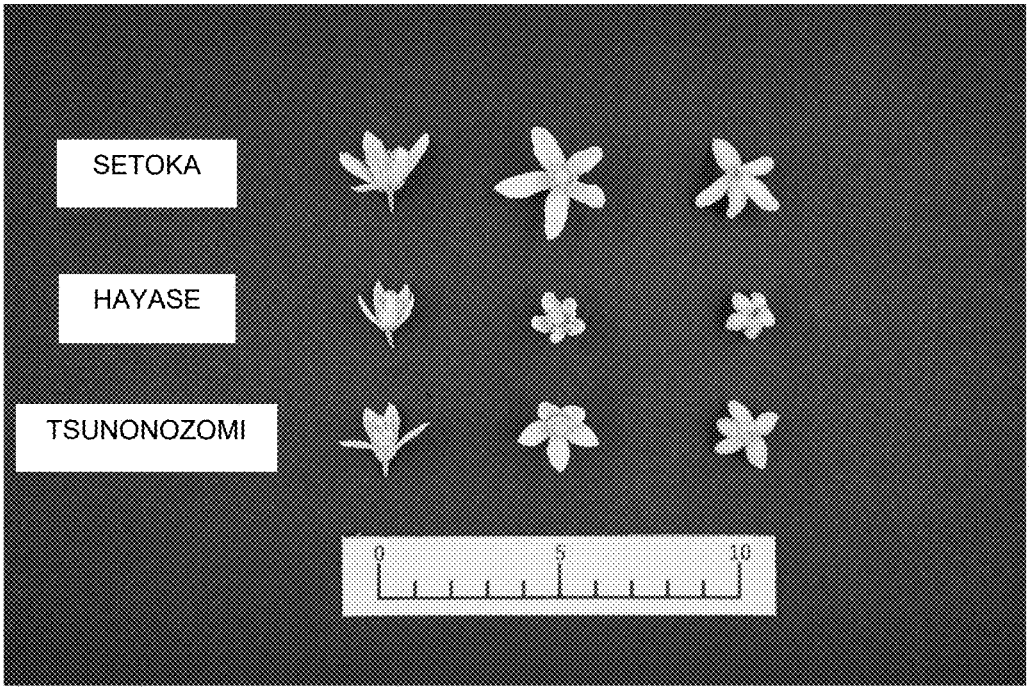
FIG. 6 is a color photograph showing flowers of 'HAYASE', together with flowers of 'SETOKA' (male parent and comparative variety) and 'TSUNONOZOMI' (female parent).
Figure 7:
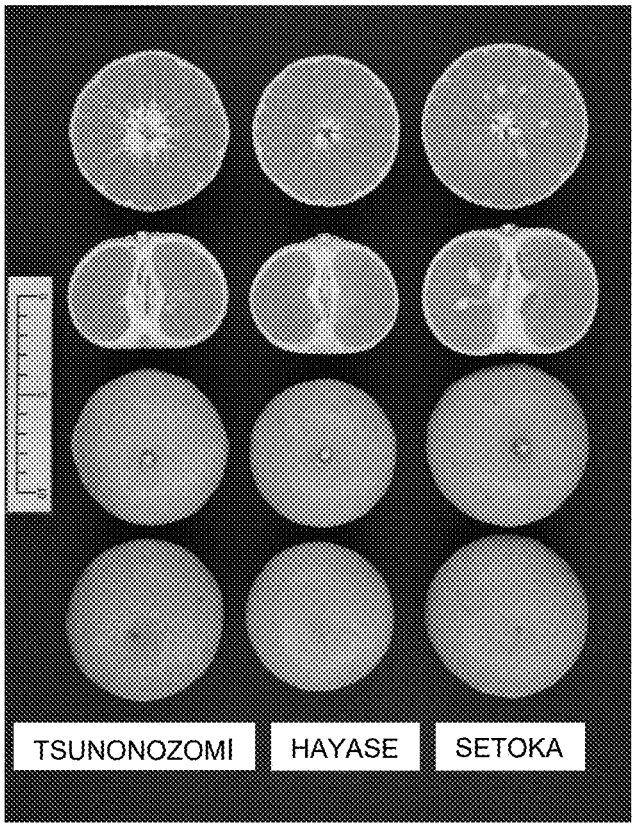
FIG. 7 is a color photograph showing the horizontal section, the transverse section, upper view and lower view of a fruit of 'HAYASE' together with a fruit of female parent 'TSUNONOZOMI', and male parent 'SETOKA', illustrating the difference between the fruit apex shape, in that the fruit of 'HAYASE' has a flat apex, whereas the fruit of 'TSUNONOZOMI' has a sinking apex.
Figure 8:
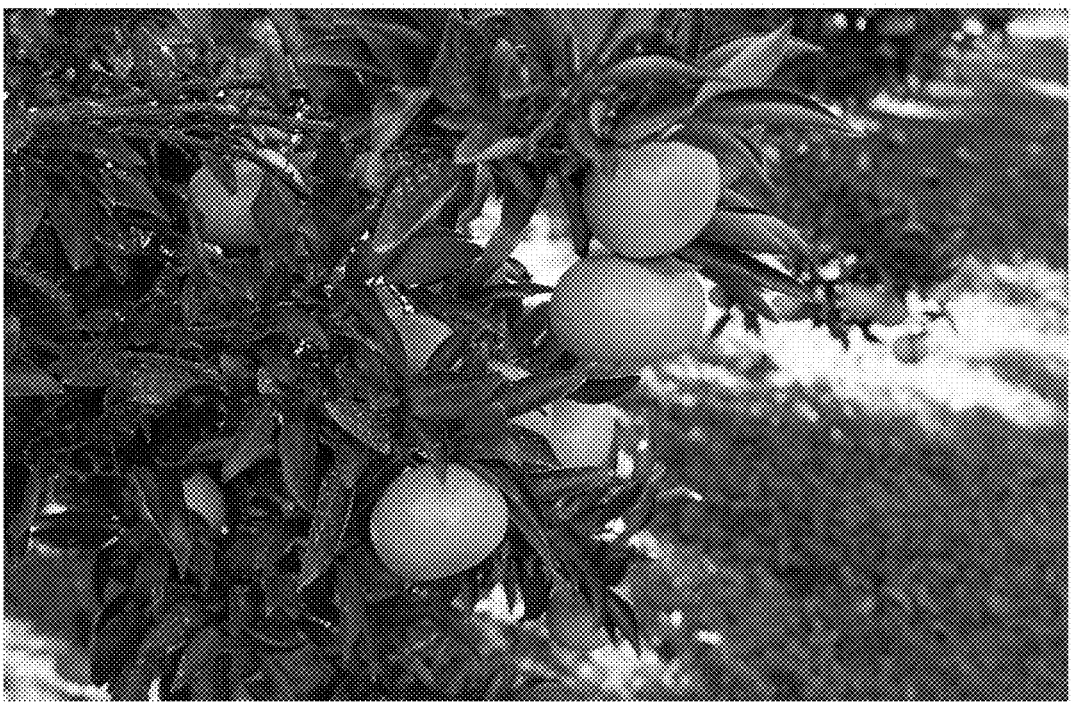
FIG. 8 is a color photograph showing a fruiting state on the tree of 'HAYASE'.
Figure 9:
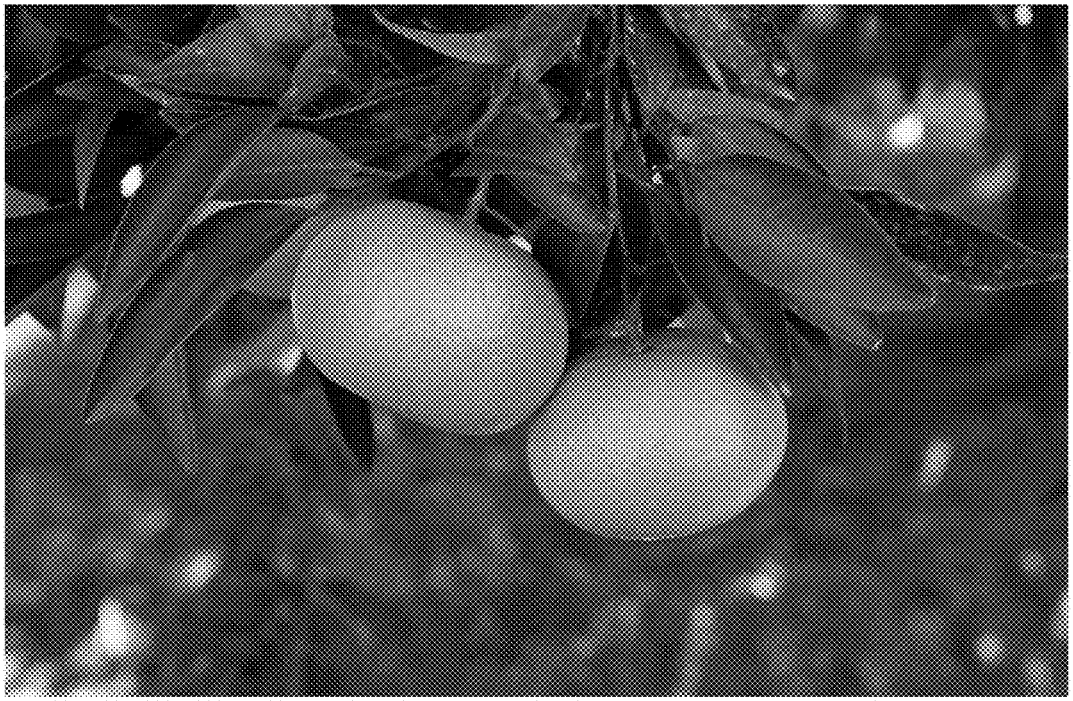
FIG. 9 is another color photograph showing a fruiting state on the tree of 'HAYASE'.

Due to chemical and/or digital development, processing and printing, the plants or portions of plants depicted in the photographs may or may not be precisely accurate, when compared to the actual botanical specimens.

DETAILED DESCRIPTION OF THE INVENTION

Table 3 below shows the botanical description of the 'HAYASE' plants evaluated in 2022 and 2023 (including the comparison with the reference plant 'SETOKA'). The values provided are averages. The ages of the trees evaluated was 7 years, and the location of the trees evaluated was Shizuoka-city, Shizuoka, Japan.

The 'HAYASE' plants shown on the photographs were grown at Shizuoka-city, Shizuoka, Japan. The plants were 7-year grown trees after top grafting. The tree was photographed on Nov. 24, 2023, the flowers were photographed on Apr. 30, 2023, and the fruits were photographed on Jan. 5, 2023.

Colors are given according to the J.H.S. (Japan Horticultural Society) Color Chart.

BOTANICAL DESCRIPTION

TABLE 5

Botanical description of 'HAYASE'

| No. | Characteristics | Descriptions | Values |
|---|---|---|---|
| 1. | Tree habit | in-between upright and spreading | |
| 2. | Shoot density | dense | |
| 3. | Tree size: average height | | 2.3 m |
| 4. | Tree size: average spread | | 2.4 m |
| 5. | Tree vigor | medium | |
| 6. | One year old shoot: diameter | medium | 2.7 mm |
| 7. | One year old shoot: length | medium | 11.9 cm |
| 8. | One year old shoot: internode | medium | 1.7 cm |
| 9. | One year old shoot: spine (number of spines per leaf nodes) (%) | few | 5% |
| 10. | Spine: average size | very short | 1.9 mm |
| 11. | Spine: average color | dull greenish yellow | JHS 2910 |
| 12. | Leaf blade: shape | spindle shaped | |
| 13. | Leaf blade: apex shape | acuminate | |
| 14. | Leaf blade: base shape | acute | |
| 15 | Leaf blade: wave | weak | |
| 16. | Leaf blade: size | medium | 21.1 cm2 |
| 17. | Leaf blade: length | medium | 8.2 cm |
| 18 | Leaf blade: width | narrow | 3.5 cm |
| 19. | Leaf shape (length/width ratio) | medium | 2.4 |
| 20. | Leaf thickness | medium | 0.34 mm |
| 21. | Leaf vein: clarity of upper surface | slightly clear | |
| 22. | Leaf vein: color of upper surface | soft yellow green | JHS 3310 |

TABLE 5-continued

Botanical description of 'HAYASE'

| No. | Characteristics | Descriptions | Values |
|---|---|---|---|
| 23. | Leaf color: upper surface | dark green | JHS 4007 |
| 24. | Leaf color: lower surface | soft green | JHS 3709 |
| 25. | Wing shape | vestigial | |
| 26. | Wing length | medium | 13.9 mm |
| 27. | Wing width | narrow | 3.2 mm |
| 28. | Petiole length | medium | 17.7 mm |
| 29. | Petiole diameter (base) | medium | 1.5 mm |
| 30. | Petiole color | soft yellow green | JHS 3511 |
| 31. | Peduncle color | soft yellow green | JHS 3511 |
| 32 | Inflorescence | single | |
| 33. | Flower weight (beginning of flowering) | light | 0.23 g |
| 34. | Petal shape (full flowering) | lanceolate | |
| 35. | Petal length (full flowering) | short | 10.9 mm |
| 36. | Petal width (full flowering) | narrow | 4.9 mm |
| 37. | Petal color (full flowering, outside) | yellowish white | JHS 2902 |
| 38. | Petal number | 5 | |
| 39. | Pistil average length | short | 7.9 mm |
| 40. | Stamen average length | short | 6.3 mm |
| 41. | Stamen: average color of anther | yellowish white | JHS 2701 |
| 42. | Filament number | few | 17.3 |
| 43. | Filament separation | separating | |
| 44. | Pollens | none | |
| 45. | Ovary shape | compressed | |
| 46. | Style shape | straight | |
| 47. | Fruit: average diameter | medium | 70.1 mm |
| 48. | Fruit: average height | medium | 52.5 mm |
| 49. | Fruit: shape of proximal part | flattened | |
| 50. | Fruit: diameter/height ratio | high | 1.34 |
| 51. | Fruit: shape of distal part | flattened | |
| 52. | Fruit: broadest part | at middle | |
| 53. | Fruit: radial groove at distal part | absent | |
| 54. | Fruit: apex concave ring (circular depression or disk-shaped protuberance around the style scar) | absent | |
| 55. | Fruit: radial groove at proximal part | very few | 0.6 |
| 56 | Fruit: stalk end depression | absent | |
| 57. | Fruit: collar | absent | |
| 58. | Fruit: shape in transverse section | circular | |
| 59. | Fruit: areola | absent | |
| 60. | Core density | sparse | |
| 61. | Core size (core diameter/fruit diameter) | small | 19.1 |
| 62. | Fruit weight | medium | 149.9 g |
| 63. | Skin color | bright orange | JHS 1305 |
| 64. | Albedo color | pale reddish orange | JHS 2202 |
| 65. | Oil gland size | mixed, including small, medium, and large | |
| 66. | Oil gland number | medium | 66.8 cm2 |
| 67. | Oil gland surface | convex | |
| 68. | Fruit surface | smooth to medium | |
| 69. | Fruit surface glossiness | medium | |
| 70. | Amount of albedo adhering to fruit flesh (not including fruit strands) | small | |
| 71. | Fruit navel (when viewed internally) | absent | |
| 72. | Fruit average number of segments | many | 13 |
| 73. | Fruit average number of rudimentary segments | absent or few | |
| 74. | Peel thickness | thin | 2.0 mm |
| 75. | Pericarp percentage | small | 16.1% |
| 76. | Peeling | easy to medium | |
| 77. | Septum firmness | soft | |
| 78. | Juice sacs shape | medium | |
| 79. | Juice sacs size | medium | |

TABLE 5-continued

Botanical description of 'HAYASE'

| No. | Characteristics | Descriptions | Values |
|---|---|---|---|
| 80. | Flesh color | deep orange | JHS 1307 |
| 81. | Juiciness of flesh | juicy | |
| 82. | Sweetness | high | 13.6 (Brix) |
| 83. | Bitterness | not bitter | |
| 84. | Acidity | low | 0.90 g/ 100 ml |
| 85. | Seeds/fruit (since there are very few, the seed characteristics were not measured) | very few | 0.8 on average |
| 86. | Embryo color (multigerm only) | pale yellow green | JHS 3102 |
| 87. | Polyembryony | present | |
| 88. | Sprouting time | medium | early April |
| 89. | Flowering time | medium | early May |
| 90. | Flowering habit | flowering once | |
| 91. | Time of maturity | early | January |
| 92. | Fruit shipping quality | moderate | |
| 93. | Fruit storage life | moderate | 1-2 months |

TABLE 5-continued

Botanical description of 'HAYASE'

| No. | Characteristics | Descriptions | Values |
|---|---|---|---|
| 94. | Fruit market use | as fresh fruit | |
| 95. | Fruit market productivity | | 40 kg/plant |

OTHER FEATURES OF THE PLANT ARE AS FOLLOWS

Disease and pest resistance: normal resistance was observed for pests and diseases in Shizuoka-city, Shizuoka Japan, in particular the following pests: thrips, fruit-piercing stink bugs, scales; and the following diseases: *Citrus* canker, melanose, botrytis fruit injury.

Tree hardiness: USDA Hardiness Zone: 9a-9b.

We claim:

1. A new and distinct variety of *Citrus* sp. tree named 'HAYASE', substantially as described and illustrated herein.

* * * * *